(12) United States Patent
Dwoskin et al.

(10) Patent No.: US 6,455,543 B1
(45) Date of Patent: Sep. 24, 2002

(54) CIS-2,6-DISUBSTITUTED PIPERIDINES FOR THE TREATMENT OF PSYCHOSTIMULANT ABUSE AND WITHDRAWAL, EATING DISORDERS, AND CENTRAL NERVOUS SYSTEM DISEASES AND PATHOLOGIES

(75) Inventors: Linda P. Dwoskin; Peter A. Crooks; Marlon D. Jones, all of Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/628,557

(22) Filed: Jul. 28, 2000

Related U.S. Application Data

(60) Provisional application No. 60/146,144, filed on Jul. 30, 1999.

(51) Int. Cl.[7] ................... A61K 31/445; C07D 211/18; C07D 211/20
(52) U.S. Cl. ................... 514/317; 546/194; 546/236
(58) Field of Search ................. 546/194, 195, 546/236; 514/317, 330, 331

(56) References Cited

U.S. PATENT DOCUMENTS

| | | | |
|---|---|---|---|
| 5,414,005 A | 5/1995 | Schneider et al. | |
| 5,486,362 A | 1/1996 | Kitchell et al. | |
| 5,830,904 A | 11/1998 | Crooks et al. | |
| 6,087,376 A | * 7/2000 | Crooks et al. | ............... 514/317 |

FOREIGN PATENT DOCUMENTS

| | | |
|---|---|---|
| FR | 2 528 834 | 6/1982 |

OTHER PUBLICATIONS

The Condensed Chemical Dictionary 1956 Fifth Edition p. 110.*

The Practice of Medicinal Chemistry, Camille G. Wermuth, Adacemic Press, 1996, pp. 204–205.

Database CAS on STN, (Columbus, OH, USA) Accession No. 103:88116 "Lobelanine" CS217195, (1982).

Database CAS on STN, (Columbus, OH, USA) Accession No. 123:37615 Schiffrin et al. "Electroassisted separation of metals by solvent extraction and supported–liquid memberanes", Hydrometall. '94, Int. symp. (1994).

Database CAS on STN, (Columbus, OH, USA) Accession No. 66:22229, Kracmar et al. "Ultraviolet spectrophotometry in the control of drugs" Pharmazie (1966).

Database CAS on STN, (Columbus, OH, USA) Accession No. 72:65748, Schoenenberger et al. "Action mechanism of antimicrobial beta–amino ketones", Phar. Acta helv.(1996) vol. 44, No. 11, pp. 691–714.

Database CAS on STN, (Columbus, OH, USA) Accession No. 128:270483, Katritzky et al. "A short asymmetric synthesis of 2,5–disubstituted pyrrolidines", Tetrahedron Lett (1998) vol. 39, pp. 1698–1700.

* cited by examiner

Primary Examiner—Alan L. Rotman
Assistant Examiner—Rita Desai
(74) Attorney, Agent, or Firm—McDermott, Will & Emery

(57) ABSTRACT

Cis-2,6-disubstituted piperdine analogs, or lobeline analogs, having the general formula:

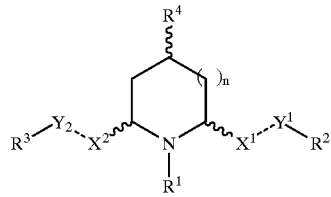

are used to treat diseases of the central nervous system, drug abuse and withdrawal therefrom as well as to treating eating disorders.

18 Claims, No Drawings

CIS-2,6-DISUBSTITUTED PIPERIDINES FOR THE TREATMENT OF PSYCHOSTIMULANT ABUSE AND WITHDRAWAL, EATING DISORDERS, AND CENTRAL NERVOUS SYSTEM DISEASES AND PATHOLOGIES

This application claims the benefit of Provisional Application No. 60/146,144, filed on Jul. 30, 1999.

FIELD OF THE INVENTION

The present invention relates to lobeline analogs, specifically cis-2,6-disubstituted piperidines, and their method of use in the treatment of diseases and pathologies of the central nervous system (CNS), the treatment of drug abuse and withdrawal therefrom as well as to the treatment of eating disorders such as obesity.

BACKGROUND OF THE INVENTION

Alpha-Lobeline (lobeline), a lipophilic nonpyridino, alkaloidal constituent of Indian tobacco, is a major alkaloid in a family of structurally-related compounds found in Lobelia inflata. Lobeline has been reported to have many nicotine like effects, including tachycardia and hypertension (Olin et al., 1995), hyperalgesia (Hamann et al., 1994) and improvement of learning and memory (Decker et al., 1993). Lobeline has high affinity for nicotinic receptors (Lippiello et al., 1986; Broussolle et al., 1989). However, no obvious structural resemblance of lobeline to nicotine is apparent and structure function relationships between S(-)-nicotine and lobeline do not suggest a common pharmacophore (Barlow et al., 1989). Also, differential effects of lobeline and nicotine suggest that these drugs may not be active through a common CNS mechanism, even though lobeline has been considered a mixed nicotinic agonist/antagonist.

Lobeline evokes dopamine (DA) release from rat striatal slices. However, lobeline evoked DA release is neither dependent upon extracellular calcium nor is it sensitive to mecamylamine, a noncompetitive nicotinic receptor antagonist. Thus, lobeline evoked DA release occurs via a different mechanism than does nicotine to evoke DA release (Teng et al., 1997, 1998; Clarke et al., 1996). In this respect, lobeline also inhibits DA uptake into rat striatal synaptic vesicles via an interaction with the dihydrotetrabenazine (DTBZ) site on vesicular monoamine transporter-2 (VMAT2), thus increasing the cytosolic DA available for reverse transport by the plasma membrane transporter (DAT) (Teng et al., 1997, 1998). Thus, lobeline interacts with nicotinic receptors and blocks nicotine-evoked DA release, but also interacts with DA transporter proteins to modify the concentration of DA in the cytosolic and vesicular storage pools, thereby altering subsequent dopaminergic neurotransmission.

SUMMARY OF THE INVENTION

The present invention is directed to a method of treating an individual who suffers from a disease or pathology of the central nervous system (CNS) or for treating an individual for drug dependence or withdrawal for drug dependence. The method comprises administering to the individual an effective amount of a cis-2,6-substituted piperidino compound, i.e., a lobeline analog, including pharmaceutically acceptable salts of such compounds thereof. As used herein, an "effective amount" refers to an amount of a drug effective to reduce an individual's desire for a drug of abuse or for food, or for alleviating at least one of the symptoms of the disease or pathological symptom of a CNS pathology. The compound can be administered alone, combined with an excipient, co-administered with a second drug having a similar or synergistic effect. The compound is administered subcutaneously, intramuscularly, intravenously, transdermally, orally, intranasally, intrapulmonary or rectally. The use of cis-2,6-disubstituted piperidines and derivatives thereof in treating diseases or pathologies of the CNS is implicated. In particular, the treatment of dependencies of such drugs as cocaine, amphetamine, caffeine, nicotine, phencyclidine, opiates, barbiturates, benzodiazepines, canabinoids, hallucinogens, and alcohol is implicated. Also, the treatment of eating disorders such as obesity is implicated.

In a preferred aspect of the invention, the method of treatment reduces an individual's desire for the drug of abuse or for food by at least one day, but it is also preferred that the treatment method further comprise administering behavior modification counseling to the individual. Although the compound of the present invention is contemplated primarily for the treatment of drug abuse and withdrawal and for eating disorders, other uses are also suggested by the studies discussed herein. Thus, cognitive disorders, brain trauma, memory loss, psychosis, sleep disorders, obsessive compulsive disorders, panic disorders, myasthenia gravis, Parkinson's disease, Alzheimer's disease, schizophrenia, Tourette's syndrome, Huntington's disease, attention deficit disorder, hyperkinetic syndrome, chronic nervous exhaustion, narcolepsy, motion sickness and depression, and related conditions are considered to be susceptible to treatment with a compound of the present invention.

As shown by the results of the studies described herein, lobeline analogs are found to be effective in inhibiting uptake of extracellular DA by cells of the CNS. Some of these analogs are a also nicotinic receptor antagonists. Either or both mechanisms can thereby work to alter the distribution of the intracellular DA pools and as a result alter extracellular DA concentration.

As used herein the term "lobeline" refers to a compound having the general chemical formula 2-[6-(β-hydroxyphenethyl)-1-methyl-2-piperidyl]-acetophenone. The term "lobeline analogs" and equivalents thereof as used herein, refers to chemical derivatives of lobeline obtained by oxidation or reduction of lobeline, others obtained by esterification of lobeline and redox derivatives, as well as various substitutions at the N-position of the piperidinyl moiety.

DETAILED DESCRIPTION OF THE INVENTION

The 2,6-disubstituted piperidine lobeline analogs of the present invention include those contemplated by the following formula (I), without regard to chirality:

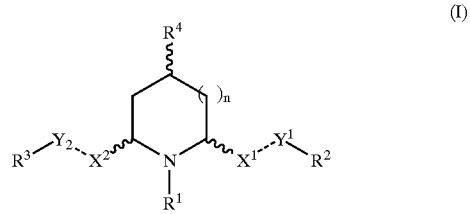

(I)

wherein:
n is zero or an integer in the range from 1 to 3;
$X^1$ - - - $Y^1$ and $X^2$ - - - $Y^2$ are the same or are independently different from one another and represent a saturated carbon-carbon bond, a cis-carbon-carbon double bond, a trans-carbon-carbon double bond, a carbon-carbon triple bond; a saturated sulfur-carbon bond, a saturated selenium-carbon bond, an oxygen-carbon bond, a saturated nitrogen-carbon bond, a N-alkyl substituted saturated nitrogen-carbon bond where said alkyl is a lower straight chain or branched alkyl, a nitrogen-carbon double bond, or a nitrogen-nitrogen double bond;

$R^1$ and $R^4$ are the same or are independently different from one another and represent hydrogen or a lower straight chain or branched alkyl or $R^1$ and $R^4$ together form a ring including a —$CH_2$—, —$CH_2CH_2$—, —$CH_2CH_2$—$CH_2$—, —cis—CH=CH, —cis—$CH_2$—CH=CH—or —cis—$CH_2$=CH—$CH_2$— moiety;

$R^2$ and $R^3$ are the same or are independently different from one another and represent a saturated or unsaturated hydrocarbon ring; a nitrogen containing heterocyclic moiety; an oxygen containing heterocyclic moiety; a sulfur containing heterocyclic moiety; a selenium containing heterocyclic moiety; a mixed heterocyclic moiety containing at least two atoms selected from the group consisting of nitrogen, oxygen and sulfur; and an ortho, meta or para-substituted benzene;

with the proviso that when n=0, $R^2$ and $R^3$ are unsubstituted phenyl groups, and $X^1$ - - - $Y^1$ and $X^2$ - - - $Y^2$ are saturated carbon-carbon bonds, $Y^1$ cannot be $CH_2$, CHOH or C=O, and $Y^2$ cannot be $CH_2$, CHOH, or C=O.

It is preferred that when $R^3$ and/or $R^4$ is a saturated hydrocarbon ring, the ring includes, but is not limited to, cyclobutane, cyclopentane, cyclohexane, cycloheptane or cyclooctane, including all possible substitution patterns, geometric and stereoisomers, racemic, diastereomeric and enantiomeric forms thereof.

It is further preferred that when $R^3$ and/or $R^4$ is an unsaturated hydrocarbon ring, the ring includes, but is not limited to, benzene, cyclopentene, cyclohexene, cycloheptene, cyclooctene or cyclopentadiene, including all possible substitution patterns, geometric and stereoisomers, racemic, diastereomeric and enantiomeric forms thereof.

It is further preferred that when $R^3$ and/or $R^4$ is a nitrogen containing heterocyclic moiety, the moiety includes, but is not limited to, azetine, piperdine, piperazine, pyrazine, pyrazole, pyrazolidine, imidazole imidazoline, pyrimidine, hexa-hydropyrimidine, pyrrole, pyrrolidine, triazine, 1,2,3-triazole, 1,2,4-triazole, pyridine or pyridazine, including all possible substitution patterns, geometric and stereoisomers, racemic, diastereomeric and enantiomeric forms thereof.

It is further preferred that $R^3$ and/or $R^4$ is an oxygen containing heterocyclic moiety, the moiety includes, but is not limited to, furan, tetrahydrofuran, 2,5-dihydrofuran, pyran, tetrahydropyran, 1,4-dioxane, 1,3-dioxane or 1,4-oxathinin, including all possible substitution patterns, geometric and stereoisomers, racemic, diastereomeric and, enantiomeric forms thereof.

It is further preferred that when $R^3$ and/or $R^4$ is a sulfur containing heterocyclic moiety, the moiety includes, but is not limited to, thietane, thiophene, thiophane, 2,5-dihydrothiophene, 1,3-dithiolylium, 1,3-dithiolane, 1,2-dithiolylium, 1,2-dithiolane, thiane, 1,2-dithiane, 1,3-dithane, 1,4-dithiane, or thiopyranylium, including all possible substitution patterns, geometric and stereoisomers, racemic, diastereomeric and enantiomeric forms thereof.

It is further preferred that when $R^3$ and/or $R^4$ is a selenium containing heterocyclic moiety, the moiety includes, but is not limited to, selenophene, including all possible substitution patterns, geometric and stereoisomers, racemic, diastereomeric and enantiomeric forms thereof.

It is further preferred that when $R^3$ and/or $R^4$ is a mixed heterocyclic moiety, the moiety includes, but is not limited to, thiazolidine, thiazole and oxazin, including all possible substitution patterns, geometric and stereoisomers, racemic, diastereomeric and enantiomeric forms thereof.

The substituted benzene includes at least one substituent, where the substituent is selected from , but is not limited to, the group consisting of methyl, ethyl, propyl, isopropyl, butyl, sec-butyl, isobutyl, amino, N-methylamino, N,N-dimethylamino, carboxylate, methylcarboxylate, ethylcarboxylate, propylcarboxylate, isopropylcarboxylate, carboxaldehyde, acetoxy, propionyloxy, isopropionyloxy, cyano, aminomethyl, N-methylaminomethyl, N,N-dimethylaminomethyl, carboxamide, N-methylcarboxamide, N,N-dimethylcarboxamide, acetyl, propionyl, formyl, benzoyl, sulfate, methylsulfate, hydroxyl, methoxy, ethoxy, propoxy, isopropoxy, thiol, methylthio, ethylthio, propiothiol, fluoro, chloro, bromo, iodo, trifluoromethyl, vinyl, allyl, propargyl, nitro, carbamoyl, ureido, azido, isocyanate, thioisocyanate, hydroxylamino and nitroso.

It is preferred that when either $X^1$ - - - $Y^1$ or $X^2$ - - - $Y^2$ is a saturated carbon-carbon bond, $Y^1$ or $Y^2$ represents $CH_2$, CH—OH, CHO-alkyl where said alkyl is a lower straight chain or branched alkyl, CH—$OSO_2$—$C_6H_5$, CH—$OSO_2$-p-$C_6H_4CH_3$, CH—SH, $C_6H_5$—SH, CH—S-alkyl where said alkyl is a lower straight chain or branched alkyl, CH—$NO_2$, CH—$CF_3$, CH—NHOH, CH—OCHO, CH—F, CH—Cl, CH—Br, CH—I, CH—$NH_2$, CH—NH-alkyl where said alkyl is a lower straight chain or branched alkyl, CH—N(alkyl)$_2$ where said alkyl is a lower straight chain or branched alkyl, CH—$OCONH_2$, CH—OCONH-alkyl where said alkyl is a lower straight chain or branched alkyl, CH—OCON(alkyl)$_2$ where said alkyl is a lower straight chain or branched alkyl, CH—$N_3$, C=O or C=S; CH—O-aryl such as a phenyl, ortho-, meta-, or para-substituted phenyl where the substituent is as described above; or a hydrocarbon or hetercyclic ring such as pyridyl, furanyl, naphthyl, thiazole, selenothenyl, oxazolyl, 1,2,3-triazole, 1,2,4-triazole, imidazoline, pyrimidine, pyridazine or triazine, including all possible substitution patterns, diastereomeric and enantiomeric forms thereof.

The lower straight or branched alkyl can be an alkyl group containing one to seven carbon atoms. The preferred alkyl groups are methyl and ethyl.

The above 2,6-substituted piperidino analogs are preferred in their cis-geometrical isomeric forms, or in their trans geometric forms, including all possible geometric, racemic, diastereiomeric, and enantiomeric forms thereof.

The above cis-2,6-disubstituted piperidines as well as analogs thereof can be administered in their free base form or as a soluble salt. Whenever it is desired to employ a salt of a cis-2,6-substituted piperidine or its analog, it is preferred that a soluble salt be employed. Some preferred salts include hydrochloride, hydrobromide, nitrate, sulfate, phosphate, tartrate, galactarate, fumarate, citrate, maleate, glycolate, malate, ascorbate, lactate, aspartate, glutamate, methanesulfonate, p-toluenesulfonate, benzenesulfonate, salicylate, proprionate, and succinate salts. The above salt forms may be in some cases hydrates or solvates with alcohols and other solvents.

A pharmaceutical composition containing a compound of the invention is also contemplated, which may include a conventional additive, such as a stabilizer, buffer, salt, preservative, filler, flavor enhancer and the like, as known to those skilled in the art. Representative buffers include phosphates, carbonates, citrates and the like. Exemplary preservatives include EDTA, EGTA, BHA, BHT and the like. A composition of the invention may be administered by inhalation, i.e., intranasally as an aerosol or nasal formulation; topically, i.e., in the form of an ointment, cream or lotion; orally, i.e., in solid or liquid form (tablet, gel cap, time release capsule, powder, solution, or suspension in aqueous or non aqueous liquid; intravenously as an infusion or injection, i.e., as a solution, suspension or emulsion in a pharmaceutically acceptable carrier; transdermally, e.g., via a transdermal patch; rectally as a suppository and the like.

Generally, the pharmacologically effective dose of a present compound is in the amount ranging from about $1 \times 10^{-5}$ to about 1 mg/kg body weight/day. The amount to be administered depends to some extent on the lipophilicity of the specific compound selected, since it is expected that this property of the compound will cause it to partition into fat deposits of the subject. The precise amount to be administered can be determined by the skilled practitioner in view of desired dosages, side effects and medical history of the patient and the like.

The cis-2,6-disubstituted piperidino analogs of the present invention exhibit selectivity for either neuronal nicotinic acetylcholine receptors and/or the dopamine transporter protein (DAT). The derivatives that are active towards the nicotinic receptor generally do not interact with the DAT, and those that interact with the DAT show only modest nicotinic receptor activity.

TABLE 1

(II)

[Structure diagram showing piperidine with phenyl groups, substituents $Y^2$, $X^2$, $S$, $R$, $X^1$, $Y^1$, and N-CH$_3$]

| Compound | Ki ($\mu$M) [$^3$H]-Nicotine Binding Assay | Ki ($\mu$M) [$^3$H]-Dopamine Uptake Assay |
|---|---|---|
| 1. $X^1 = X^2 = CH_2$<br>$Y^1 = C=O$<br>$Y^2 = (S)$—CHOH | 0.0043 | 45 |
| 2. $X^1 = X^2 = Y^1 = Y^2 = CH_2$ | 14.3 | 3.0 |
| 3. $X^1 = X^2 = CH_2$<br>$Y^1 = C=O$<br>$Y^2 = (S)$—CHOSO$_2$—C$_6$H$_4$-p-CH$_3$ | 0.0041 | 39 |
| 4. $X^1 = X^2 = CH_2$<br>$Y^1 = Y^2 = C=O$ | 11 | 25 |
| 5. $X^1, Y^1 = X^2, Y^2 =$ trans CH=CH | >100 | 0.8 |
| 6. $X^1 = CH_2$<br>$Y^1 = C=O$<br>$X^2, Y^2 =$ trans CH=CH | 0.13 | 3.0 |
| 7. $X^1 = X^2 = CH_2$<br>$Y^1 = (S)$—CHOH<br>$Y^2 = (R)$—CHOH | 0.93 | 54 |
| 8. $X^1 = X^2 = Y^2 = CH_2$<br>$Y^1 = (RS)$—CHOH | 0.16 | 8.9 |
| 9. $X^1 = CH_2$<br>$Y^1 = (S)$—CHOH<br>$X^2, Y^2 =$ trans CH=CH | 4.2 | 1.3 |

The nine cis-2,6-disubstituted piperidino derivatives listed in Table 1 have the chemical structure of formula (II). They were assayed for nicotinic receptor interaction and inhibition of DAT activity. The cis-2,6-disubstituted piperidino analogs of the present invention exhibit selectivity for either neuronal nicotinic acetylcholine receptors and/or the dopamine transporter protein (DAT). The derivatives that are active towards the nicotinic receptor generally do not interact with the DAT, and those that interact with the DAT show only modest nicotinic receptor activity.

The nine compounds in Table 1 were evaluated in the high affinity [$^3$H]nicotine binding assay and afforded inhibition constants (Ki values) ranging from 0.0043 $\mu$M to >100 $\mu$M. Five of these compounds were in the range of 4–160 nM. Three of these compounds were in the range of 0.93–14 FM. One compound was >100 RM. The cis-2,6-disubstituted piperidino derivatives listed in Table 1 were also assayed for inhibition of DAT activity, i.e., inhibition of [$^3$H]DA uptake into the dopaminergic presynaptic terminal. Nine compounds were evaluated and afforded inhibition constants (Ki values) ranging from 0.08 $\mu$M to 54 $\mu$M.

Removal of both functionalities of the lobeline molecule resulted in loss of affinity for the nicotinic receptor and a 100-fold more potent inhibition of the dopamine transporter compared with lobeline. Removal of either the hydroxyl group or the keto group of lobeline resulted in a 50-fold loss of affinity for the nicotinic receptor. Interestingly, the ketoalkene analog inhibited DAT 10-fold more potently than lobeline, whereas lobelanidine inhibited DAT equipotently compared to lobeline. Conversion of the hydroxy group of lobeline to a bulky tosyloxy group reduced the affinity of the nicotinic receptor by only 3-fold, but did not alter the interaction with the DA transporter. The hydroxyalkene had a similar potency with the meso-transdiene (the most potent compound) in the DA uptake assay, but had 1000-fold lower affinity for the nicotinic receptor. Also, the completely defunctionalized lobeline molecule and the hydroxyalkane analog were both less potent than the meso-transdiene in inhibiting DA uptake into striatal synaptosomes. This data indicates that appropriate structural modification of the lobeline molecule affords compounds in which the interaction with DAT is enhanced. Furthermore, in one compound, i.e., the meso-transdiene, the nicotinic receptor interaction has been eliminated and the compound is thus selective for inhibition of DAT.

The invention will now be discussed by certain examples that illustrate but do not limit the invention.

EXAMPLE 1

Cis-2,6-di-trans-Styrylpiperidine 1.00 g (2.95 mmol) of lobelanidine was dissolved in 15 ml of 85% H$_3$PO$_4$ and allowed to stir overnight at 60° C. The reaction mixture was taken up in H$_2$O and made basic with solid K$_2$CO$_3$ (pH~8). The pH was adjusted by the addition of solid NaOH (pH~10). The aqueous solution was extracted three times with 15 ml of EtOAc. The organic layers were? combined and dried over anhydrous MgSO$_4$. The salts were removed via filtration and solvent removed by rotary evaporation affording 0.70 g of crude product. This compound was recrystallized from MeOH affording 0.60 g of pure cis-2,6-di-trans-styrylpiperidine. Percent yield =78.6% Mp=139–141° C. $^1$H NMR (300 MHz, CDCl$_3$) d: 1.40–1.80 (m, 6H), 2.23 (s, 3H), 2.50–2.64 (t, 2H), 6.04–6.20 (dd, 2H), 6.39–6.50 (d, 2H) and 7.10–7.38 (m, 10H); $^{13}$C NMR (CDCl$_3$) d: 23.75, 33.56, 42.32, 68.36, 126.26, 127.38, 128.61, 130.52,133.89 and 137.13 ppm.

EXAMPLE 2

Cis-2S,6R, 8S-2-[(6-(βpara-Toluenesulfonyloxvphenethyl)-1-methyl-2-piperidyl]-acetophenone 1.00 g (2.58 mmol) of lobeline hemisulfate was dissolved in 25 ml. of pyridine and was added dropwise to a solution (cooled to 0° C.) containing 0.60 g (3.14 mmol) of p-toluenesulfonyl chloride dissolved in 15 ml of pyridine. After addition, the reaction was allowed to stir for 2 hours and then poured into 50 ml of ice-cold water and the mixture was stirred for an additional two hours. The aqueous solution was extracted three times with 25 ml of EtOAc. The organic layers were combined and dried over anhydrous $Na_2SO_4$. The salts were removed by filtration and the solvent was removed by rotary evaporation affording 450 mg of a pink-colored compound. The product was recrystallized from acetone yielding 300 mg of the product. Percent yield=21.6% mp=169.1–171.0° C. $^1$H NMR (300 MHz, $CDCl_3$) δ: 1.30–1.98 (m, 6H), 2.20 (s, 3H), 2.63–2.74 (d, 3H), 2.95–3.20 (m, 2H), 3.61–3.78 (d, 1H), 3.83–4.12 (m, 2H), 450–4.72 (m, 1H), 4.80–4.90 (d, 1H), 6.90–7.00 (d, 2H), 7.10–7.50 (m, 8H), 7.50–7.60 (d, 2H), 7.80–7.90 (d, 2H) and 9.85 (s, 1H); $^{13}$C NMR ($CDCl_3$) δ: 21.16, 22.25, 23.32, 23.55, 27.35, 38.29, 40.18, 40.07, 60.79, 63.69, 71.05, 125.56, 125.76, 127.39, 128.28, 128.44, 128.69, 128.77, 133.67, 133.96,135.87, 140.03, 141.98,144.47 and 195.21 ppm.

EXAMPLE 3

Cis-2S,6R-N-Methyl-6-phenacyl-2-trans-styrylpiperidine 1.00 g (2.58 mmol) of lobeline hemisulfate was dissolved in 15 ml of 85% $H_3PO_4$ and the solution was allowed to stir for 24 hrs at 50° C. Phosphoric acid was, then neutralized with $K_2CO_3$, and a little ice cold $H_2O$ was added to dissolve the salts. The aqueous solution was extracted with ethyl acetate (20 ml×3). The organic layers were combined and dried with anhydrous $MgSO_4$. The salts were removed by filtration and the solvent was removed via rotary evaporation, affording 0.80 g of a gummy solid, which contained mainly the trans isomer. Percent yield=84.6%. $^1$H NMR (300 MHz, $CDCl_3$) 1.15–1.60 (m, 6H), 2.02 (s, 3H), 2.47(m, 3H), 3.16–3.34 (dd, 1H), 5.80–6.00 (dd, 1H), 6.18–6.28 (d, 1H), and 6.90–7.38 (m. 8H) and 7.64–7.80 (d, 2H); $^{13}$C NMR ($CDCl_3$) 23.52, 32.56, 33.17, 40.52, 44.02, 5.9.62, 68.08, 126.00, 127.15, 127.92, 128.36, 128.44, 130.29, 132.91, 133.91, 136.95, 136.99 and 198.83 ppm.

EXAMPLE 4

Cis-10R,2S,6R- and Cis-10S,2S,6R-N-Methyl-6-[1-(2-hydroxy-2-phenyl)-ethyl]-2-trans-styryliperidine In a 250 ml round bottom flask was added 0.80 g of cis-2S,6R-N-methyl-6-phenacyl-2-trans-styrylpiperidine, and 50 ml of ethanol. Sodium borohydride was added until all of the starting material was consumed (determined by TLC). The solution was cooled to 0° C. and acetone was added in small portions to quench the reaction. The solvents were evaporated to dryness and water was added precipitating 0.75 g of an off-white crystalline solid (1:1) mixture of diastereomers, which was purified on silica eluting with 75:25 (CHCl3/EtOH). The yield of the product (a mixture of diastereomers) was 93.4%. $^1$H NMR (300 MHz, $CDCl_3$) δ: 1.17–2.06 (m, 12H), 2.12 (s, 3H), 2.35 (s, 3H), 2.50–6.20 (m, 4H), 2.70–3.20 (m, 4H), 4.78–4.80 (dd, 1H), 5.04–5.14 (dd, 1H), 5.96–6.20 (m, 2H), 6.32–6.42 (dd, 2H) and 7.04–7.34 (m, 20H); $^{13}$C NMR ($CDCl_3$) δ: 23.69, 24.15, 26.74, 29.68, 33.26, 39.94, 41.10, 41.41, 62.93, 63.00, 65.62, 68.32, 71.76, 15 73.90,125.46,126.15, 126.19, 126.83, 127.01,127.37, 128.16, 128.23, 128.50, 130.58, 132.61, 133.85, 136.83, 136.95, 145.32 and 145.45 ppm.

EXAMPLE 5

Cis-2S 6R-N-Methyl-6-[1-(2-hydroxy-2-phenyl) ethyl]2-phenylethlypiperidine 0.50 g (1.55 mmol) of cis-2S,6R-N-methyl-6-phenacyl-2-trans-styrylpiperidine was dissolved in 50 ml of ethanol and placed into a Parr hydrogenation apparatus with 0.10 g of 10% Pd-on-Carbon. After removal of air, hydrogen gas was introduced until a pressure of 40 psig was reached. The reaction was allowed to proceed for 48 hrs. The Pd catalyst was removed through filtration with Celite, and ethanol was removed by rotary evaporation to afford 0.30 g of a yellow oil. The compound was purified by silica gel chromatography eluting with EtOAc to afford 0.25 g of the product. The yield was 50.0%. $^1$H NMR (300 MHz, $CDCl_3$) δ: 0.70–0.90 (m, 6H), 1.18 (s, 3H), 1.40–1.90 (m, 6H), 2.44–2.56 (m, 2H), 4.564.60 (dd, 1H) and 7.04–7.30 (m, 10H); $^{13}$C NMR ($CDCl_3$) δ: 25.77, 29.24, 29.38, 29.42, 29.46, 29.68, 31.44, 35.93, 39.07, 74.64, 125.50,125.85,127.42, 128.17,128.35, 128.37, 142.85 and 144.91 ppm.

EXAMPLE 6

High Affinity [$^3$H]Nicotine Binding Assay

The ability to displace S(-)[$^3$H]NIC binding from rat striatal membranes to assess interaction with the α4 β2 subtype was determined. The [$^3$H]NIC binding assay was performed according to previously published methods (Romano et al., 1980; Marks et al., 1986; Crooks et al., 1995). Striata from two rats were dissected, pooled and homogenized with a Tekmar polytron in 10 vol of ice-cold modified Krebs-HEPES buffer (in mM; 20 HEPES, 118 NaCl, 4.8 KCl, 2.5 $CaCl_2$, 1.2 $MgSO_4$, adjusted to pH to 7.5). The homogenate was incubated at 37° C. for 5 minutes to promote hydrolysis of endogenous acetylcholine, and centrifuged at 15,000 g for 20 minutes and the pellet was resuspended in 10 vol of ice-cold distilled water and incubated at 37° C. for 5 minutes, followed by centrifugation at 15,000 g for 20 min. The pellet containing the striatal membranes was resuspended in 10 vol of fresh ice-cold 10% Krebs-HEPES buffer and incubated at 37° C. for 10 min after which it was centrifuged at 15,000 g for 20 minutes. The latter sequence of resuspension, incubation and centrifugation was repeated. The pellet was frozen under fresh Krebs-HEPES buffer and stored at −40° C. until assay. Upon assay, the pellet was resuspended in Krebs-HEPES buffer, incubated at 37° C. for 5 minutes and centrifuged at 15,000 g for 20 min. The final pellet was resuspended in 3.6 ml ice-cold water which provides for approximately 200 μg protein/100 μl aliquot. Competition assays were performed in duplicate in a final volume of 200 μl Krebs-HEPES buffer containing 250 mM Tris buffer (pH 7.5 at 4° C.). Reactions were initiated by addition of 100 μl of membrane suspension to 3 nM [$^3$H]NIC (50 μl) and 1 of at least 9 concentrations of analog (50 μl). After 90 minutes incubation at 4° C., reactions were terminated by dilution of the samples with 3 ml of ice-cold buffer followed immediately by filtration through a Whatman GF/B glass fiber filters (presoaked in 0.5% polyethyleneimine (PEI) using a Brandel Cell Harvester. Filters were rinsed 3× with 3 ml of ice-cold buffer, transferred to scintillation vials and 5 ml scintillation cocktail added. Nonspecific binding was defined as binding in the presence of 10 μM NIC. For competition curves, the $IC_{50}$ values were corrected for ligand concentration (Cheng et al., 1973).

EXAMPLE 7

[$^3$H]Dopamine ([$^3$H]DA) Uptake Assay, Striatal Synaptosomal Preparation

[$^3$H]DA uptake was performed according to a modification of the previously reported methods (Dwoskin et al., 1999). Striata were homogenized in 20 ml of ice-cold sucrose solution (0.32 M sucrose and 5 mM sodium bicarbonate, pH 7.4) with 12 passes of a teflon-pestle homogenizer (clearance approximately .003 in). The homogenate was centrifuged at 2,000 g, 4° C. for 10 min. The supernatant was centrifuged at 12,000 g, 4° C, for 20 minutes. The resulting pellet was resuspended in 1.5 ml ice-cold assay buffer (in mM; 125 NaCl, 5 KCl, 1.5 $KH_2PO_4$, 1.5 $MgSO_4$, 1.25 $CaCl_2$, 10 glucose, 0.1 L-ascorbate, 25 HEPES, 0.1 EDTA and 0.1 pargylin pH 7.4). The final protein concentration was 400 μg/ml. Assays were performed in duplicate in a total vol of 500 μl. Aliquots (50 μl synaptosomal suspension containing 20 pg of protein) were added to assay tubes containing 350 μl buffer and 50 μl of 1 of 9 concentrations (final concentration, 1 nM–1 mM) of analog or vehicle. Synaptosomes were preincubated at 34° C. for 10 min before the addition of 50 μl of [$^3$H]DA (30.1 Ci/mmole, final concentration 10 nM) and accumulation proceeded for 10 min at 34° C. High affinity uptake was defined as the difference between accumulation in the absence and presence of 10 μM GBR 12935. Preliminary studies demonstrated that at 10 minutes [$^3$H]DA uptake is within the linear range of the time-response curve when experiments are performed at 34° C. Accumulation was terminated by addition of 3 ml ice-cold assay buffer containing 1 mM pyrocatechol and rapid filtration through a Whatman GF/B glass fiber filter paper (presoaked with buffer containing 1 mM pyrocatecol) using a Brandel Cell Harvester. The filters were washed 3 times with 3 ml of 10 ml ice-cold buffer containing 2 mM pyrocatechol, and then transferred to scintillation vials and radioactivity determined (Packard Model B1600TR scintillation counter, Meriden, Conn.). Protein concentration was determined using bovine serum albumin as the standard (Bradford, 1976). Competition curves for analog inhibition of [$^3$H]DA uptake were generated. Nonlinear regression analysis was used to fit curves either in the absence or presence of 9 concentrations of analog. IC50 values were corrected for concentration of [$^3$H]DA (Cheng-Prusoff, 1973) to yield true inhibition constants (Ki=IC50/[1+c/Km]), where c is the concentration of free [$^3$H]DA and Km is the concentration of analog at which half maximal [$^3$H]DA uptake is achieved. These values (Ki) were converted to pKi before statistical analysis.

In the examples listed in the Table, a series of cis-2,6-disubstituted piperidines, structurally related to lobeline, were synthesized and tested for activity in the high affinity nicotinic receptor binding assay and the dopamine uptake assay to assess the interaction of these piperidines with these specific proteins on the presynaptic terminal of dopaminergic neurons in the CNS. Some of these compounds have greater selectivity for interaction with DAT than for interaction with nicotinic receptors, whereas other compounds interact with both nicotinic receptors and DAT, more similar to lobeline. Other compounds were more selective for the nicotinic receptor than for DAT. These combinations of pharmacological activity are considered to be beneficical for the treatment of psychostimulant abuse and withdrawal, eating disorders, and central nervous system diseases and pathologies.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalence thereof may be resorted to, falling within the scope of the invention claimed.

REFERENCES

The pertinent disclosures of the references listed below and as discussed above herein are incorporated herein by reference.

Barlow R. B. et al., "Relations between structure and nicotine-like activity: X-ray crystal structure analysis of (−)cystine and (−)lobeline hydrochloride and a comparison with (−)nicotine and other nicotine-like compounds," Br. J. Pharmacol., 1989; 98: 799–808.

Broussolle E. P. et al., "In vivo binding of $^3$H-nicotine in the mouse brain," Life Sciences, 1989; 44: 1123–1132.

Cheng Y. C. et al., "Relationship between the inhibition constant (Ki) and the concentration of inhibitor which causes 50 percent inhibition ($I_{50}$) of an enzymatic reaction," Biochem. Pharmacol., 1973; 22: 3099–3108.

Clarke P. B. S. et al., "Release of [$^3$H]noradrenaline from rat hippocampal synaptosomes by nicotine: mediation by different nicotinic receptor subtypes from striatal [$^3$H] dopamine release," Br. J. Phanmacol., 1993; 45: 571–576.

Crooks P. A. et al., "Inhibition of nicotine-evoked dopamine release by pyridino-N-substituted nicotine analogues: a new class of nicotinic antagonist," Drug Dev. Res., 1995; 36: 71–82.

Decker M. W. et al., "Effects of lobeline, a nicotinic receptor agonist, on learning and memory," Pharmacol. Biochem. Behav. 1993; 45: 571–576.

Dwoskin L. P. et al., "S-(-)-Cotinine, the major brain metabolite of nicotine, stimulates nicotinic receptors to evoke [$^3$H]dopamine release from rat striatal slices in a calcium-dependent 30 manner," J. Pharmacol. Exp. Therap., 1999; 288: 905–911.

Hamann S. R. et al., "Hyperalgesic and analgesic actions of morphine, U50-488, naltrexone, and (−)lobeline in the rat brainstem," Pharmacol. Biochem. Behav., 1994; 47: 197–201.

Lippiello P. M. et al., "The binding of L[$^3$H]nicotine to a single class of high affinity sites in rat brain membrane," Mol. Pharmacol., 1986; 29: 448–454.

Marks M. J. et al., "Nicotine binding sites in rat and mouse brain: comparison of acetylcholine, nicotine and α-bungarotoxin," Mol. Pharmacol., 1986; 30: 427–436.

Olin B. R. et al., Drug Facts and Compansons, JB Lippincott Co., St. Louis, Mo., pp 3087–3095 (1995).

Romano C. et al., "Stereospecific nicotinic receptors on rat brain membranes," Science, 1980; 210: 647–650.

Teng L. H. et al., "Lobeline and nicotine evoke [$^3$H]-overflow from rat striatal slices preloaded with [$^3$H] dopamine: differential inhibition of synaptosomal and vesicular [$^3$H]dopamine uptake," J. Pharmacol. Exp. Therap., 1997; 80: 1432–1444.

Teng L. H. et al, "Lobeline displaces [$^3$H] dihydrotetrabenazine binding and releases [$^3$H]dopamine from rat sriatal synaptic vesicles," J. Neurochem., 1998; 71: 258–265.

What is claimed is:

1. A cis-2,6-substituted piperidino compound or pharmaceutically effective salt thereof comprising formula (I):

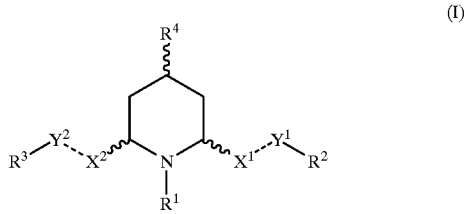

wherein:
- $X^1$ - - - $Y^1$ and $X^2$ - - - $Y^2$ are the same or are independently different from one another and represent a saturated carbon-carbon bond, $X^1$ and $X^2$ represent $CH_2$ or $CH=CH$, and $Y^1$ and $Y^2$ represent $CH_2$ or $CH=CH$, $C=O$ or $CHOH$;
- $R^1$ and $R^4$ are the same or are independently different from one another and represent hydrogen or a lower straight chain or branched alkyl; and
- $R^2$ and $R^3$ are the same or are independently different from one another and represent a saturated or unsaturated hydrocarbon ring;
- with the proviso that when $R^2$ and $R^3$ are unsubstituted phenyl groups, $Y^1$ and $Y^2$ cannot be CHOH or C=O.

2. The compound of claim 1, wherein the saturated hydrocarbon ring includes cyclobutane, cyclopentane, cyclohexane, cycloheptane or cyclooctane.

3. The compound of claim 1, wherein the unsaturated hydrocarbon ring includes benzene, cyclopentene, cyclohexene, cycloheptene, cyclooctene or cyclopentadiene.

4. The compound of claim 1, wherein the pharmaceutical salts are hydrochloride, hydromide, sulfate, hydrosulfate, citrate, fumarate or tartrate salts of said compound.

5. The compound of claim 1, wherein said lower straight chain or branched alkyl contains one to seven carbon atoms.

6. The compound of claim 5, wherein said alkyl is methyl or ethyl.

7. The compound of claim 1, herein said compound is cis-2S,6R-N-methyl-6-[1-(2-hydroxy-2-phenyl)ethyl]-2-phenylethylpiperdine.

8. A method of treating an individual for dependence on a drug of abuse, withdrawal from a drug of abuse, for an eating disorder, or for a CNS disease or pathology comprising administering to the individual an effective amount of a cis-2,6-substituted piperidino compound or pharmaceutically effective salt thereof comprising formula (I):

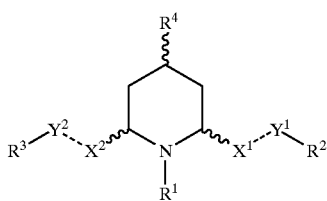

(I)

wherein said administering of the compound inhibits uptake of dopamine by cells of the central nervous system of the individual and wherein:
- $X^1$ - - - $Y^1$ and $X^2$- - - $Y^2$ are the same or are independently different from one another and represent a saturated carbon-carbon bond, $X^1$ and $X^2$ represent $CH_2$ or $CH=CH$, and $Y^1$ and $Y^2$ represent $CH_2$ or $CH=CH$, $C=O$ or $CHOH$;
- $R^1$ and $R^4$ are the same or are independently different from one another and represent hydrogen or a lower straight chain or branched alkyl; and
- $R^2$ and R3 are the same or are independently different from one another and represent a saturated or unsaturated hydrocarbon ring;
- with the proviso that when $R^2$ and R3 are unsubstituted phenyl groups, $Y^1$ and $Y^2$ cannot be CHOH or C=O.

9. The method of claim 8, wherein the saturated hydrocarbon ring includes cyclobutane, cyclopentane, cyclohexane, cycloheptane or cyclooctane.

10. The method of claim 8, wherein the unsaturated hydrocarbon ring includes benzene, cyclopentene, cyclohexene, cycloheptene, cyclooctene or cyclopentadiene.

11. The method of claim 8, wherein the pharmaceutical salts are hydrochloride, hydrobromide, sulfate, hydrosulfate, citrate, fumarate or tartrate salts of said compound.

12. The method of claim 8, wherein said lower straight chain or branched alkyl contains one to seven carbon atoms.

13. The method of claim 8, wherein said alkyl is methyl or ethyl.

14. The method of claim 8, wherein said compound is cis-2S,6R-N-methyl-6-[-(1-2-hydroxy-2-phenyl)ethyl]-2-phenylethylpiperdine.

15. The method of claim 8, wherein said compound is cis-2,6-di-trans-styrylpiperdine.

16. The method of claim 8, wherein said compound is cis-2S,6R-N-methyl-6-phenacyl-2-trans-styrylpiperdine.

17. The method of claim 8, wherein said compound is cis-10R,2S,6R-N-methyl-6-[-2(-hydroxy-2-phenyl)-ethyl]-2-trans-styrylpiperdine.

18. The method of claim 8, wherein said compound is cis-10S,2S,6R-N-methyl-6-[1I-2(-hydroxy-2-phenyl)-ethyl]-2-trans-styrylpiperdine.

* * * * *

UNITED STATES PATENT AND TRADEMARK OFFICE
CERTIFICATE OF CORRECTION

PATENT NO. : 6,455,543 B1
DATED : September 24, 2002
INVENTOR(S) : Linda P. Dwoskin et al.

It is certified that error appears in the above-identified patent and that said Letters Patent is hereby corrected as shown below:

Column 3,
Lines 30, 36, 42, 50, 57 and 65, "$R^3$ and/or $R^4$" should read -- $R^2$ and/or $R^3$ --.

Column 4,
Line 3, "$R^3$ and/or $R^{4"}$" should read -- $R^2$ and/or $R^3$ --.

Signed and Sealed this

Seventh Day of September, 2004

JON W. DUDAS
*Director of the United States Patent and Trademark Office*